United States Patent [19]

Lowe et al.

[11] Patent Number: 5,340,926
[45] Date of Patent: Aug. 23, 1994

[54] PROCESS FOR THE RECOVERY OF RECOMBINANTLY PRODUCED PROTEIN FROM INSOLUBLE AGGREGATE

[75] Inventors: Peter A. Lowe; Fiona A. O. Marston; Sarojani Angal, all of Reading; Joyce A. Schoemaker, London, all of United Kingdom

[73] Assignee: Celltech, Limited, United Kingdom

[21] Appl. No.: 102,697

[22] Filed: Aug. 5, 1993

Related U.S. Application Data

[63] Continuation of Ser. No. 726,638, Jul. 2, 1991, abandoned, which is a continuation of Ser. No. 411,255, Sep. 25, 1989, abandoned, which is a continuation of Ser. No. 676,192, Nov. 20, 1984, abandoned.

[30] Foreign Application Priority Data

Mar. 25, 1983 [GB] United Kingdom ................ 8308234
Oct. 12, 1983 [GB] United Kingdom ................ 8327345

[51] Int. Cl.$^5$ .......................... C07K 3/12; C07K 15/06
[52] U.S. Cl. ........................... 530/423; 530/300; 530/305; 530/387.1; 530/412; 530/422; 435/71.1; 435/71.2; 435/69.1; 435/226; 435/252.3; 435/252.33
[58] Field of Search ............. 435/71.1, 71.2, 69.1, 435/226, 252.3, 252.33; 530/300, 305, 387.1, 412, 422, 423

[56] References Cited

U.S. PATENT DOCUMENTS

| | | | |
|---|---|---|---|
| 4,511,502 | 4/1985 | Builder et al. | 530/417 |
| 4,656,255 | 4/1987 | Seely | 530/412 |
| 4,721,673 | 1/1988 | Uren et al. | 435/183 |
| 4,831,120 | 5/1989 | Aviv et al. | 530/399 |
| 4,935,354 | 6/1990 | Hayenga et al. | 435/69.1 |
| 4,975,529 | 1/1990 | Frazier et al. | 530/399 |
| 4,997,916 | 3/1991 | Aviv et al. | 530/399 |
| 5,064,943 | 11/1991 | McCoy et al. | 530/399 |

FOREIGN PATENT DOCUMENTS

| | | |
|---|---|---|
| 0068691 | 1/1983 | European Pat. Off. . |
| 2100737 | 1/1983 | United Kingdom . |
| 2138004 | 10/1984 | United Kingdom . |
| 8304418 | 12/1983 | World Int. Prop. O. . |

OTHER PUBLICATIONS

Zgirski et al. 1983 Acta Biochimica Bolonica 30: 33–38.
Muluihill, D. et al., *Chem Abst.* vol. 87, No. 19, p. 216, Abst. No. 147755e, Nov. 7, 1977.
Aknori, S. et al., *Chem. Abst.,* vol. 97, No. 19, p. 528, Abst No. 1608005, Nov. 8, 1982.
Wetzel, R. et al., *Gene,* vol. 16, pp. 63–71, 1981.
Wetzel, R. et al., *Biochemistry,* vol. 19 pp. 6096–6104, 1980.
Freedman, R. et al., *The Enzymology of Post Transcriptional Modification of Proteins,* vol. 1, pp. 166–170, 1980.
Mahler, M. et al *Biological Chemistry* (2nd Ed) Harper & Row, New York, N.Y., 177–183, 1971.

*Primary Examiner*—Richard A. Schwartz
*Assistant Examiner*—J. LeGuyader
*Attorney, Agent, or Firm*—Woodcock Washburn Kurtz Mackiewicz & Norris

[57] ABSTRACT

In a process for the production of a soluble native protein, such as immunoglobulin or methionine-prochymosin, in which an insoluble form of the protein is produced by a host organism transformed with a vector including a gene coding for the protein, the insoluble form of the protein is reversibly denatured in an alkaline aqueous solution at a pH selected to promote dissociation of a group or groups of the protein involved in maintaining the conformation of the protein, and the protein is subsequently allowed to renature by reducing the pH of the solution below a pH effective to denature the protein to produce the soluble native form of the protein. The pH of the alkaline aqueous is suitably in the range 9.0 to 11.5.

14 Claims, No Drawings

PROCESS FOR THE RECOVERY OF RECOMBINANTLY PRODUCED PROTEIN FROM INSOLUBLE AGGREGATE

This is a continuation of application Ser. No. 07/726,638, filed Jul. 2, 1991, now abandoned, which is a continuation of Ser. No. 07/411,255, filed Sep. 25, 1989, now abandoned; which is a continuation of application Ser. No. 06/676,192 filed Nov. 20, 1984, now abandoned, which is the U.S. National application of PCT application PCT/GB84/00093 filed Mar. 23, 1984.

FIELD OF THE INVENTION

This invention relates to the field of protein production using recombinant DNA biotechnology. In particular it relates to a process for the recovery of a protein produced in an insoluble form by a host organism transformed with a vector including a gene coding for the protein.

BACKGROUND OF THE INVENTION

There are now numerous examples of commercially valuable proteins which may be produced in large quantities by culturing a host organism capable of expressing heterologous genetic material. Once a protein has been produced by a host organism it is usually necessary to treat the host organism in some way, in order to obtain the desired protein. In some cases, such as in the production of interferon in Escherichia coli a lysis or permeabilisation treatment alone may be sufficient to afford satisfactory yields. However, some proteins are produced within a host organism in the form of insoluble protein aggregates which are not susceptible to extraction by lysis or permeabilisation treatment alone. It has been reported that a human insulin fusion protein produced in E. coli forms insoluble protein aggregates (see D. C. Williams et al (1982) Science 215 687–689).

A protein exists as a chain of amino acids linked by peptide bonds. In the normal biologically active form of a protein (hereinafter referred to as the native form) the chain is folded into a thermodynamically preferred three dimensional structure, the conformation of which is maintained by relatively weak interatomic forces such as hydrogen bonding, hydrophobic interactions and charge interactions. Covalent bonds between sulphur atoms may form intramolecular disulphide bridges in the polypeptide chain, as well as intermolecular disulphide bridges between separate polypeptide chains of multisubunit proteins, e.g. insulin. The insoluble proteins produced in some instances do not exhibit the functional activity of their natural counterparts and are therefore in general of little use as commercial products. The lack of functional activity may be due to a number of factors but it is likely that such proteins produced by transformed host organisms are formed in a conformation which differs from that of their native form. They may also possess unwanted intermolecular disulphide bonds not required for functional activity of the native protein in addition to intramolecular disulphide bonds. The altered three dimensional structure of such proteins not only leads to insolubility but also diminishes or abolishes the biological activity of the protein. It is not possible to predict whether a given protein expressed by a given host organism will be soluble or insoluble.

In our copending British Patent Application GB2100737A (an identical disclosure of which is contained in assignee's U.S. application Ser. No. 389,063, filed Jun. 16, 1982 now abandoned) we describe a process for the production of the proteolytic enzyme chymosin. The process involves cleaving a chymosin precursor protein produced by a host organism which has been transformed with a vector including a gene coding for the relevant protein. In the course of our work we discovered that the chymosin precursor proteins were not produced in their native form but as an insoluble aggregate. In order to produce a chymosin precursor in a native form which may be cleaved to form active native chymosin, the proteins produced by a host organism were solubilised and converted into their native form before the standard techniques of protein purification and cleavage could be applied.

In our copending published International Patent Application WO 83/04418 the methods used for the solubilisation of chymosin precursor proteins are described. In general the techniques described involve the denaturation of the protein followed by the removal of the denaturant thereby allowing renaturation of the protein. In one example the denaturant used is a compound such as urea or guanidine hydrochloride. When the insoluble precursor is treated with urea or guanidine hydrochloride it is solubilised. When the denaturant is removed, for example by dialysis, the protein returns to a thermodynamically stable conformation which, in the case of chymosin precursors, is a conformation capable of being converted to active chymosin.

The solubilised protein may be separated from insoluble cellular debris by centrifugation or filtration. The production of proteins from suitably transformed host organisms is potentially of great commercial value. The processes involved are of a type which may be scaled up from a laboratory scale to an industrial scale. However, where the protein produced is formed as an insoluble aggregate, potential complications in the process may increase the cost of production beyond a viable level. The solubilisation technique described above, whilst effective to solubilise such proteins, is relatively expensive and may represent a significant production cost.

We have discovered a generally applicable solubilisation process which, in its broadest aspect, does away with the requirement of relatively expensive reagents.

SUMMARY OF THE INVENTION

According to the present invention we provide a process for the production of a soluble native protein in which an insoluble form of the protein is produced by a host organism transformed with a vector including a gene coding for the protein, wherein the insoluble form of the protein is reversibly denatured in an alkaline aqueous solution at a pH selected to promote dissociation of a group or groups of the protein involved in maintaining the conformation of the protein and the protein is subsequently allowed to renature by reducing the pH of the solution below a pH effective to denature the protein to produce the soluble native form of the protein.

The use of an alkali solution to denature the insoluble protein reduces the reagent cost of the process. The pH is selected with reference to the protein to which the process is to be applied. In particular the pH is selected such that groups responsible for holding the protein in an unnatural conformation by means of intramolecular, or potentially in the case of a protein aggregate non-functional intermolecular, bonds or forces are dissociated such that, when the pH is reduced, the protein refolds in the native conformation. The groups responsible for holding the protein in an unnatural conformation may be ionisable groups, in which case the pH is preferably selected to be compatible with the pKa of the relevant ionizable group.

Studies in our laboratory have shown that intermolecular disulphide bonds exist in prochymosin aggregates produced in *E. coli* (Schoemaker et al (1984) submitted to PNAS). Native prochymosin is monomeric and contains three intramolecular disulphide bonds (Foltmann et al (1977) Proc. Natl. Acad. Sci. U.S.A. 74 pp 2321-2324). Six thiol groups per molecule are therefore available to form intermolecular and intramolecular bonds within the protein aggregate. Consequently, disulphide bonds must be broken and correctly reformed for denaturation/renaturation to successfully solubilise prochymosin. This may be achieved by using an alkaline aqueous solution of pH 10.7 ($\pm$0.5). The free thiol groups of cysteine have a pKa value of 10.46.

The term "insoluble" as used herein means in a form which, under substantially neutral conditions (for example pH in the range 5.5 to 8.5), is substantially insoluble or is in an insolubilised association with insoluble material produced on lysis of host organism cells. The insoluble product is either produced within the cells of the host organism in the form of insoluble relatively high molecular weight aggregates or may simply be associated with insoluble cell membrane material. The process permits the separation of solubilised protein from insoluble cellular debris.

Any suitable alkali may be used in the process, for example an aqueous solution of an alkali metal hydroxide such as NaOH or KOH, an aqueous buffer, or an aqueous solution of an organic base such as triethylamine.

Preferably the alkaline aqueous solution has a pH of from 9 to 11.5, most preferably from 10 to 11.

The treatment of an insoluble protein with an alkaline aqueous solution may not, in all cases, result in complete solubilisation of the protein. Since insoluble material is present at all times, a number of mass transfer effects may be important. It has been found that multiple extractions with alkali are more efficient than a single extraction even when large extraction volumes are used. This also has the advantage of minimising the time for which the solubilised protein is in contact with alkali. Preferably, therefore, one or more extractions of denatured protein are performed.

The methods of solubilisation in a strong denaturant such as guanidine hydrochloride or urea described in published British patent application GB2100737A and in published International patent application WO 83/04418 and the methods of solubilisation using alkali, according to the broad aspect of the present invention each solubilise significant percentages of insoluble proteins found in extracts from host organisms. However, neither is completely quantitative in terms of recovery of native protein. The reasons for this have not been clearly defined and are probably different for the two types of solubilisation. It appears that guanidine hydrochloride solubilises all the material present but only a portion is converted into native proteins after removal of guanidine hydrochloride. Alkali treatment may not allow complete renaturation to form the native form of the protein and in addition does not solubilise all of the insoluble form of the protein. We have discovered that by combining the two methods a greatly enhanced yield of native protein may be obtained.

According to a preferred aspect of the invention the insoluble form of the protein is first denatured in an aqueous solution, and subsequently the resulting solution is diluted in an alkaline aqueous solution at a pH selected to promote dissociation of the group or groups of the protein involved in maintaining the conformation of the protein and the protein is renatured by reducing the pH of the solution below a pH effective to denature the protein, to produce the soluble native form of the protein.

The dilution introduces an element of physical separation between the denatured molecules, before renaturation is brought about, for example, by neutralisation of the alkaline denaturing solution. The dilution and resulting physical separation of the denatured molecules appears to assist their renaturation in native form. The solubilisation process described immediately above leads to a recovery, in the case of methionine-prochymosin, of more than 30% compared to, for example, 10 to 20% for the multiple alkali extractions also described above.

Preferably the pH of the alkaline aqueous solution is from 9 to 11.5, most preferably from 10 to 11.

Preferably the dilution is from 10 fold to 50 fold. (That is a dilution into a total volume of from 10 to 50 volumes).

Preferably, in the combined solubilisation process described above the insoluble protein is denatured in an aqueous solution comprising urea at a concentration of at least 7M or in a solution comprising guanidine hydrochloride at a concentration of at least 6M.

The insoluble protein may be a recombinant animal protein produced by a host organism. Examples of such proteins are immunoglobin light and heavy chain polypeptides, foot and mouth disease antigens and thymosin and insulin proteins.

The host organism may be a naturally occuring organism or a mutated organism capable of producing an insoluble protein. Preferably, however, the host organism is an organism or the progeny of an organism which has been transformed using recombinant DNA techniques with a heterologous DNA sequence which codes for the production of a protein heterologous to the host organism and which is produced in an insoluble form. The host organism may be a eukaryotic organism such as a yeast or animal or plant cell. Preferred yeasts include *Saccharomyces cerevisiae* and *kluyveromyces*. In the alternative the host organism may be a bacterium such as *E. coli*, *B. subtilis*, *B. stearothermophilis* or *Pseudomonas*. Examples of specific host organism strains include *E. coli* HB101, *E.coli* X1776, *E.coli* X2882, *E.coli* PS410, *E. coli* RV308 and *E.coli* MRC1.

The host organism may be transformed with any suitable vector molecule including plasmids such as colE1, pCR1, pBR322, RP4 and phage $\lambda$ DNA or derivatives of any of these.

Prior to treatment with the process of the present invention the host cells may be subjected to an appropriate lysis or permeabilisation treatment to facilitate recovery of the product. For example, the host organism may be treated with an enzyme, for example a lysozome, or a mechanical cell destructing device to break down the cells.

The process of the invention may then be employed to solubilise the insolubilised product and the resulting solution may be separated from solid cell material such as insoluble cell membrane debris. Any suitable method including filtration or centrifugation may be used to separate solution containing the solubilised protein from the solid cell material.

The present invention is now illustrated by way of the following Examples:

EXAMPLE 1

An experiment was conducted in which the solubilisation of insoluble methionine-prochymosin produced by *E. coli* cells transformed with vector pCT70 was achieved using alkaline denaturation. The preparation of the transformed *E.coli* cell line is described in detail in published British patent application GB2100737A.

Frozen *E.coli*/pCT 70 cells grown under induced conditions were suspended in three times their own weight of of 0.05M Tris-HCl pH 8, 1 mM EDTA, 0.1M NaCl, containing 23 µg/ml phenylmethylsulphonylfluoride (PMSF) and 130 µg/ml of lysozyme and the suspension was incubated at 4° C. for 20 minutes. Sodium deoxycholate was added to a final concentration of 0.5% and 10 ug of DNA ase 1 (from bovine pancreas) was added per gram of *E.coli* starting material. The solution was incubated at 15° C. for 30 minutes by which time the viscosity of the solution had decreased markedly. The extract, obtained as described above, was centrifuged for 45 minutes at 4° C. and 10000×g. At this stage effectively all the methionine-prochymosin product was in the pellet fraction in insolubilised form, presumably as a result of aggregation or binding to cellular debris. The pellet was washed in 3 volumes of 0.01M tris-HCl. pH8, 0.1M NaCl, 1 mM EDTA at 4° C. After further centrifugation, as above, the supernatant solution was discarded and the pellet resuspended in 3 volumes of alkali extraction buffer: 0.05M $K_2$ $HPO_4$, 1 mM EDTA, 0.1M NaCl, pH 10.7 and the suspension adjusted to pH 10.7 with sodium hydroxide. The suspension was allowed to stand for at least 1 hour (and up to 16 hours) at 4° C., the pH of the supernatant adjusted to 8.0 by addition of concentrated HCl and centrifuged as above. Methionine-prochymosin, representing a substantial proportion of the methionine-prochymosin originally present in the pellet, was found to be present in the supernatant in a soluble form which could be converted to catalytically active chymosin by acidification/neutralisation activation treatment substantially as described in published British patent application GB2100737A.

We further noted that re-extraction of the debris left after the first alkali extraction liberates an equivalent amount of prochymosin. Alkali extraction may be repeated to a total of 4–5 times with the liberation of approximately equivalent levels of proychmosin at each extraction.

EXAMPLE 2

An experiment was conducted in which the solubilisation of an insoluble immunoglobulin light chain polypetptide produced by *E.coli* cells transformed with vector pNP3 was achieved using alkaline denaturation. The preparation of the transformed *E.coli* cell line is described in copending international patent application No. PCT/GB 84/00094, field March, 1984 (the U.S. national application of which is Ser. No. 06/672,265, filed Nov. 14, 1984, now U.S. Pat. No. 4,816,397) of even date herewith. *E.coli* cells transformed with the plasmid pNP3, containing a gene coding for the $\lambda_1$ light chain of the 4-hydroxy-3-nitrophenyl acetyl (NP) binding monoclonal antibody S43, were grown under inducing conditions. The cells were harvested and resuspended in 0.05M TRIS pH 8.0, 0.233M NaCl. 5% glycerol v/v containing 130 µg/ml of lysozyme and incubated at 4° C. or room temperature for 20 minutes. Sodium deoxycholate was then added to a final concentration of 0.05% and 10 µg of DNA ase 1 (from bovine pancreas) was added per gm wet wt of *E.coli*. The solution was then incubated at 15° C. for 30 minutes by which time the viscosity of the solution had decreased markedly. The resultant mixture was then centrifuged (at 10,000×g for 15 minutes for small volumes (1 ml) or 1 hour for larger volumes). Immunoprecipitation studies indicated that the λ light chain protein was present in the insoluble fraction rather than the soluble fraction.

In order to purify the recombinant light chain, the *E.coli* pellet fraction, obtained as described above, was resuspended in a pH 11.5 buffer comprising 50 mM $K_2$ $HPO_4$, 0.1M NaCl and 1 mM EDTA. The suspension was allowed to stand for at least 1 hour (and up to 16 hours), centrifuged as above and the pH of the supernatant adjusted to 8.0 by addition of concentrated HCl. A substantial proportion of the λ light chain protein, originally present in the pellet was found to be present in the supernatant is a soluble form.

EXAMPLE 3

An experiment was conducted in which the solubilisation of methionine-prochymosin produced by *E.coli* cells transformed with vector pCT70 was achieved using denaturation with guanidine hydrochloride, followed by dilution into an alkaline solution. The preparation of the transformed cell line is described in detail in published British patent application GB2100737A.

*E.coli*/pCT 70 cell debris containing insoluble methionine-prochymosin was prepared and washed as described in Example 1 above and the following manipulations were carried out at room temperature. The cell debris was dissolved in 3–5 volumes of buffer to final concentration of 6M guanidine HCl/0.05M Tris pH8, 1 mM EDTA, 0.1 m NaCl and allowed to stand for 30 minutes–2 hours. The mixture was diluted into 10–50 volumes of the above buffer at pH 10.7 lacking guanidine HCl. Dilution was effected by slow addition of the sample to the stirred diluent over a period of 10–30 minutes. The diluted mixture was readjusted to pH 10.7 by the addition of 1M NaOH and allowed to stand for 10 minutes–2 hours. The pH was then adjusted to 8 by the addition of 1N HCl and the mixture allowed to stand for a further 30 minutes before centrifuging as above to remove precipitated proteins. The supernatant so produced contained soluble methionine-prochymosin which could be converted to catalytically active chymosin by acidification and neutralisation and purified as described in published British patent application GB2100737A. In a very similar experiment an 8M urea buffer was used in place of the 6M guanidine HCl buffer described above. The results were as described above.

EXAMPLE 4

An experiment was conducted in which the solubilisation of methionine-prochymosin produced by *E.coli* cells transformed with vector pCT 70 was achieved using a method similar to that described in Example 3. The preparation of the transformed cell line is described in detail in published British patent application GB2100737A.

*E.coli*/pCT 70 cell debris containing insoluble methionine-prochymosin was prepared and washed as described in Example 1 above and the following manipulations were carried out at room temperature. The washed pellets were suspended in a buffer containing 50 mM Tris HCl pH 8.0, 1 mM EDTA, 50 mM NaCl and 0.1 mM PMSF supplemented with 8M urea (deionized). For every 10 g weight of starting material, 90 ml of buffer were used. After 1 hour, this solution was added slowly to a buffer containing 50 mM $KH_2PO_4$ pH 10.7 containing 1 mM EDTA and 50 mM NaCl and left for at least 30 minutes. Various dilutions were made in order to establish an optimum dilution range. This proved to be a dilution in alkali of between 10 and 50 fold. The pH was maintained at pH 10.7 for the period and then adjusted to pH 8. The product was activated to give active chymosin and the level of chymosin activity was assayed (Emtage, J. S., Angal S., Doel, M. T., Harris, T. J. R., Jenkins, B., Lilley, G., and Lowe, P. A. (1983) Proc. Natl. Acad. Sci. USA 80, 3671–3675). The results are shown in Table 1.

TABLE 1

Effect of dilution on the recovery of milk clotting activity.

| FOLD DILUTION | | | MILK CLOTTING ACTIVITY |
|---|---|---|---|
| UREA | ALKALI | OVERALL | (mg) |
| 1 | 10 | 10 | 0.04 |
| 1 | 25 | 25 | 0.10 |
| 1 | 50 | 50 | 0.05 |
| 5 | 10 | 50 | 0.10 |
| 5 | 25 | 125 | 0.09 |
| 5 | 50 | 250 | 1.23 |
| 10 | 10 | 100 | 1.97 |
| 10 | 25 | 250 | 1.56 |
| 10 | 50 | 500 | 0.09 |

EXAMPLE 5

An experiment was conducted in which the solubilisation of insoluble immunoglobulin heavy and light chains produced together in *E. coli* was achieved using denaturation with urea followed by dilution into alkali. The preparation of the transformed cell line is described in copending international patent application No. PCT/GB 84 of even data herewith.

In order to produce functional antibodies from *E. coli* cells expressing the genes for both the heavy and light immunoglobulin chains, the cells were lysed, the insoluble material was washed followed by sonication (three times for 3 minutes). The material was then dissolved in 9M urea 50 mm Glycine-Na+ pH10.8 1 Mm EDTA and 20 mM 2-mercaptoethanol. This extract was dialysed for 40 hours against three changes of 20 vols. of 100 mM ECl 50 Mm Glycine-Na+ pH10.8 5% glycerol 0.5 mM EDTA 0.5 mM reduced glutathione and 0.1 mM oxidised glutathione. The dialysate was cleared by centrifugation at 30,000 g for 15 minutes and loaded directly onto DEAE sephacel followed by development with 0–0.5M KCl linear gradient in 10 mM Tris-HCl 0.5 mM EDTA pH8.0.

We claim:

1. In a process for the production of a soluble native protein which comprises the steps:

(a) culturing a host organism transformed with a vector including a gene coding for said protein to produce an insoluble aggregate form of said protein;

(b) reversibly denaturing said insoluble aggregate form of said protein by adding said insoluble aggregate form of said protein to a first solution comprising an aqueous solution of urea or guanidine hydrochloride, and (c) subsequently renaturing the protein whereby the soluble native form of said protein is produced, the improvement of enhancing the yield of native protein wherein a second solution is subsequently added to step (b) comprising an aqueous solution of an alkali metal hydroxide or an alkali metal extraction buffer, which second solution and the combined first and second solutions having a pH which dissociates groups of said protein which maintain conformation of said protein, and reducing in step (c) the pH of the combined aqueous solutions of step (b) to a level below that effective to denature the protein.

2. The process of claim 1 wherein the second solution of step b is an aqueous solution of an alkali metal hydroxide.

3. The process of claim 2 wherein the alkali metal hydroxide is sodium hydroxide.

4. The process of claim 2 wherein the alkali metal hydroxide is potassium hydroxide.

5. The process according to claim 2 wherein the volume of said second solution is from 10 to 50 times greater than the volume of said first solution, wherein said second solution has a pH from 10 to 11.5, and wherein said alkali metal hydroxide is sodium hydroxide or potassium hydroxide.

6. The process according to claim 5 wherein the first solution comprises an aqueous solution of urea at a concentration of at least 7M.

7. The process according to claim 5 wherein the first solution comprises an aqueous solution of guanidine hydrochloride at a concentration of at least 6M.

8. The process of claim 1 wherein the second solution of step b is an aqueous solution of the alkali extraction buffer $K_2HPO_4$.

9. The process of claim 1 wherein the second solution of step b is an aqueous solution of the alkali extraction buffer $KH_2PO_4$.

10. The process according to claim 1 wherein said second solution has a pH from 9 to 11.5.

11. The process according to claim 1 wherein the insoluble form of the protein is present in conjunction with debris derived from the host organism, said debris being insoluble in said second solution.

12. The process of claim 1 wherein the volume of said second solution added is from 10 to 50 times greater than the volume of the first solution.

13. The process of claim 1 wherein the first solution comprises an aqueous solution of urea at a concentration of at least 7M.

14. The process of claim 1 wherein the first solution comprises an aqueous solution of guanidine hydrochloride at a concentration of at least 6M.

* * * * *